United States Patent [19]
Tanner et al.

[11] Patent Number: 5,256,410
[45] Date of Patent: Oct. 26, 1993

[54] TREATMENT OF SQUAMOUS CELL CARCINOMA INTRALESIONALLY WITH RECOMBINANT HUMAN ALPHA INTERFERON

[75] Inventors: Daniel J. Tanner, Brooklyn; Edwin A. Peets, New York, both of N.Y.; Kenneth A. Smiles, Novato, Calif.

[73] Assignee: Schering Corporation, Kenilworth, N.J.

[21] Appl. No.: 684,964

[21] Appl. No.: 684,964

[22] PCT Filed: Nov. 29, 1989

[86] PCT No.: PCT/US89/05287
§ 371 Date: May 20, 1991
§ 102(e) Date: May 20, 1991

[87] PCT Pub. No.: WO90/06135
PCT Pub. Date: Jun. 14, 1990

Related U.S. Application Data

[63] Continuation of Ser. No. 278,315, Dec. 1, 1988, abandoned.

[51] Int. Cl.⁵ .............................................. A61K 37/66
[52] U.S. Cl. ...................................... 424/85.7; 514/21
[58] Field of Search ........................................ 424/85.7

[56] References Cited

U.S. PATENT DOCUMENTS

| | | | |
|---|---|---|---|
| 4,289,690 | 9/1981 | Pestka et al. | 260/112 R |
| 4,503,035 | 3/1985 | Pestka et al. | 424/85 |

FOREIGN PATENT DOCUMENTS

| | | |
|---|---|---|
| 0077063 | 4/1983 | European Pat. Off. |
| 32134 | 8/1984 | European Pat. Off. |
| 0248583 | 12/1987 | European Pat. Off. |
| 0305551 | 3/1989 | European Pat. Off. |

OTHER PUBLICATIONS

Lever et al. Histopatholopy of the Shin, 7ed. p. 631 (Philadelphia 1990).
Eron et al., New Engl. J. Med., vol. 315, pp. 1059–1064, 1986.
Smiles et al., The Biology of the Interferon System, Contell et al., pp. 493–501, 1986.
Acta Dermatol-Kyoto, vol. 81, No. 2, 1986, pp. 241–246 (H. Morita et al.).
Ikeda, Gan to Kagaku Ryoho, 12 (4), 936–942 (1985).
Ikic, et al., The Lancet, May 9, 1981, pp. 1025–1027.
Rubenstein, Biochem. Biophys. Acta, 695, 5–16 (1982).
Nagata, et al., Nature 284, 316–320 (1980).
Ikic, Interferon and Cancer (editor, Sikora, K) pp. 169–181, Plenum Press, New York, NY (1983).

Primary Examiner—Michael G. Wityshyn
Assistant Examiner—Choon P. Koh
Attorney, Agent, or Firm—Henry C. Jeanette; Paul A. Thompson; Gerald S. Rosen

[57] ABSTRACT

Human squamous cell carcinoma is successfully treated by intralesional administration of recombinant human interferon alfa-2b.

5 Claims, No Drawings

TREATMENT OF SQUAMOUS CELL CARCINOMA INTRALESIONALLY WITH RECOMBINANT HUMAN ALPHA INTERFERON

The present application is the United States national application corresponding to International Application No. PCT/US 89/05287, filed Nov. 29, 1989 and designating the United States, which PCT application is in turn a continuation of U.S. application Ser. No. 07/278,315, filed Dec. 1, 1988, now abandoned, the benefit of which applications is claimed pursuant to the provisions of 35 U.S.C. §§120,363 and 365(c).

BACKGROUND

This invention relates to a method of treating squamous cell carcinoma with recombinant human alpha interferon by administering the interferon directly into the carcinoma lesion, i.e. intralesionally.

Squamous cell carcinomas are cutaneous neoplasms found in humans and often arise in sun-damaged areas. Present treatment methods include various surgical techniques such as electrodesiccation and curettage, excision, cryosurgery and irradiation. Cure rates for the surgical techniques are generally quite good, however, non-surgical methods of therapy are generally thought to be more desirable.

Various efforts have been made to treat cancers by injecting interferon directly into the lesion. For example, Ikeda, Gan to Kagaku Ryoho, 12(4), 936–942 (1985) used recombinant interferon A to treat various malignant skin tumors and achieved low cure rates. None of the tumors treated were stated to be squamous cell carcinomas. Ikic et al., The Lancet, May 9, 1981, pages 1025–1027, treated squamous cell carcinoma with crude human leucocyte interferon. Ikic et al. did not use a purified interferon material, but used a material containing a mixture of leukocyte interferon components and non-interferon impurities.

Interferons are a family of proteins which exhibit antiviral activity against certain viruses and anticancer activity against certain cancers. There are three types of interferons; alpha or leukocyte interferon, beta or fibroblast interferon and gamma or immune interferon. Human alpha interferon is a naturally occurring mixture of at least eleven components including those designated alpha-1 interferon and alpha-2 interferon. Human alpha interferon exhibiting biological properties similar to those of naturally occurring human leukocyte interferon can be made by recombinant methods.

A number of alpha interferon species or components are known and are usually designated by a numeral after the Greek letter alpha, and all are contemplated for use in this invention. Thus, the species designated human alpha-1 interferon and human alpha-2 interferon (sometimes called human alpha-2 interferon which includes human alpha-2a and human alpha-2b interferon; USAN: Interferon Alfa-2 including Interferon alfa-2a and Interferon Alfa-2b) are contemplated, with human alpha-2 interferon preferred. Interferon alfa-2 can be produced in bacteria using recombinant techniques as disclosed in Rubenstein, Biochem. Biophys. Acta, 695, 5–16 (1982). In addition, interferon alfa-2 may be prepared by recombinant-DNA methods disclosed by Nagata et al., Nature, 284, 316–320 (1980), European patent 32,134 and U.S. Pat. No. 4,289,690. Various alpha-2-interferon species are disclosed in U.S. Pat. No. 4,503,035. Preferred for use in this invention is the human interferon alfa-2b (hIFN-α2b).

SUMMARY OF THE INVENTIONS

This invention relates to a method of treating squamous cell carcinoma with recombinant alpha interferon, preferably human recombinant DNA interferon alfa-2 (hIFN-α2), by administering intralesionally (by injection) to a patient in need of such treatment, a sufficient amount of human recombinant alpha interferon, preferably purified recombinant interferon alfa-2b, to be effective as an antitumor agent.

DETAILED DESCRIPTION

As used herein "alpha interferon" means recombinant alpha-1 interferon and recombinant alpha-2 interferon (sometimes referred to as interferon alfa-2). In most instances this invention will be described in the following discussion using "human recombinant interferon alfa-2", "hIFN-α2" or "hIFN-α2b".

For intralesional administration, liquid injectable pharmaceutically acceptable compositions are used. Such compositions can, for example, be prepared by diluting freeze dried hIFN-α2 with sterile preservative free water to produce an isotonic solution containing the appropriate concentration of interferon. Other injectable compositions using saline, aqueous dextrose, glycerol, ethanol and the like, to thereby form a solution or suspension for injection can also be used. If desired, minor amounts of nontoxic auxiliary substances such as wetting or emulsifying agents, preservatives, pH buffering agents and the like, for example, sodium acetate or sorbitan monolaurate, can be incorporated into the compositions. Actual methods of preparing such dosage forms are known, or will be apparent, to those skilled in this art; see for example, *Remington's Pharmaceutical Sciences*, Mack Publishing Company, Easton, Pa., 15th Edition, 1975. The amount of hIFN-α2 administered is critical only to the extent that it is effective for the therapeutic purpose. The quantity in the composition or formulation administered will, in any event, be an amount effective to achieve an antisquamous cell carcinoma effect in the subject being treated.

The amount of hIFN-α2 in a 0.15 ml. injectable dosage is about $1.5 \times 10^6$ I.U. (International Units)

In clinical tests to determine the effect of hIFN-α2 on squamous cell carcinoma, the hIFN-α2 is administered in doses of $1.5 \times 10^6$ I.U. three days a week for three weeks, i.e. $13.5 \times 10^6$ I.U. total.

Although these doses and the regimen described were beneficial, it is contemplated that they be considered only guidelines and that the attending clinician will determine, in his or her judgment, an appropriate dosage and regimen, using the patient's age and condition as well as the severity of the squamous cell carcinoma. Thus, from 0.1 to $10 \times 10^6$ I.U. hIFN-α2 can be used for each injection.

The following illustrates the effects of treating patients having squamous cell carcinoma with intralesionally administered interferon alfa-2b.

PATIENTS AND METHODS

Patients

Twenty-one patients, each with one biopsy proven cutaneous squamous cell carcinoma were included in the study. The lesions varied in size from 0.5 cm. to 2.0 cm in its largest linear dimension.

Each patient was in good health and elected to be treated with interferon alfa-2b rather than undergo other ablative or surgical procedures.

Treatment

Treatments were conducted with freeze-dried human recombinant alpha-2 interferon which was in vials and was diluted with sterile water to produce an isotonic solution containing sufficient interferon concentration so that 0.15 ml of solution contained $1.5 \times 10^6$ International Units (IU). Each lesion was injected with 0 15 ml of alpha-2 interferon using a 30-gauge needle. The needle was inserted into the lesion with care being taken to inject the entire amount intralesionally. The procedure was repeated for a total of three injections per week for three weeks. Thus, each lesion was injected with a total of $13.5 \times 10^6$ I.U.

Patients were evaluated during the treatment for clinical response and side effects. Evaluations were continued at six week intervals after completion of treatment for a total of 18 weeks.

Response Criteria

The entire treated area was excised eighteen weeks following completion of the treatment with alpha-2 interferon. Clinical responses were measured during treatment and follow-up visits through evaluation of changes in lesion size and signs and symptoms at the site of the treated lesion. The excisional specimen was carefully evaluated histologically for the presence of any residual squamous cell cancer.

The following Table I shows the results of treatment of squamous cell carcinoma with recombinant human alpha-2 interferon.

TABLE I

Results of Treating Squamous Cell Carcinoma with Interferon Alfa-2b.

Excisional biopsy results 18 weeks post-treatment

| Number of Patients | Number Cured | Number Not Cured | Observed Cure Rate | Approximate 95% Confidence Interval* |
|---|---|---|---|---|
| 21 | 20 | 1 | 95% | 72–100% |

*Fleiss, JL. Statistical Methods for Rates and Proportions. J. Wiley & Sons, NY, 1981, pp 14–15.

As is apparent from the data in Table I, no evidence of residual squamous cell carcinoma was found upon excisional biopsy in 20 of the 21 patients, giving an observed cure rate of 95%.

The sites where the squamous cell carcinomas had been treated could be identified by a slightly hypopigmented macule, sometimes with slight atrophy, and a small depressed scar from the diagnostic punch biopsy. In many of the cases, the area where the tumor had been could only be identified by the scar from the diagnostic biopsy.

SIDE EFFECTS

No life threatening or serious side effects were found. Typically, after approximately one week of treatment, a mild inflammatory reaction extending approximately 5 mm beyond the treated area was observed. Almost asymptomatic, this reaction effectively masked tumor signs and slowly regressed after treatment stopped. Ulceration beyond that originally associated with the tumors did not occur, and usually within eight weeks post-treatment neither the tumor nor the inflammatory reaction was clinically apparent.

The results of the above described program show that intralesional injection of interferon alfa-2b is a safe, effective treatment for squamous cell carcinoma, yielding excellent cosmetic results.

What is claimed is:

1. A method for treating human squamous cell carcinoma comprising intralesionally administering to a human in need of such treatment a sufficient amount of a purified recombinant human alpha-2 interferon to be effective as an anti-squamous cell carcinoma agent.

2. A method of claim 1 wherein the alpha-2 interferon is recombinant human interferon alfa-2b.

3. A method of claim 1 wherein treatment is effected by administering a dosage of 0.1 to $10 \times 10^6$ International Units of recombinant human alpha-2 interfereon by injection.

4. A method of claim 1 wherein the dosage is $1.5 \times 10^6$ International Units.

5. A method of claim 4 wherein the dosage is administered three days a week for three weeks.

* * * * *